United States Patent [19]

Benke et al.

[11] 4,278,799
[45] Jul. 14, 1981

[54] CONTINUOUS PROCESS FOR THE PRODUCTION OF DICHLOROACETAMIDES

[75] Inventors: Alan H. Benke; Hue T. Morris, both of Oakland; Louie A. Nady, Berkeley, all of Calif.

[73] Assignee: Stauffer Chemical Company, Westport, Conn.

[21] Appl. No.: 144,500

[22] Filed: Apr. 28, 1980

[51] Int. Cl.$^3$ .................. C07C 102/00; C07D 263/04
[52] U.S. Cl. ..................................... 548/215; 564/143
[58] Field of Search ................. 260/561 HL; 548/215; 564/143

[56] References Cited
U.S. PATENT DOCUMENTS

| | | |
|---|---|---|
| 3,268,324 | 8/1966 | Hamm et al. ................. 260/561 HL |
| 3,647,876 | 3/1972 | Kise et al. ..................... 260/561 HL |
| 3,884,671 | 5/1975 | Albright et al. ..................... 548/215 |
| 3,914,302 | 10/1975 | Chan et al. ..................... 260/561 HL |
| 3,959,304 | 5/1976 | Teach ................................... 548/215 |
| 4,038,284 | 6/1977 | Pitt ....................................... 548/215 |
| 4,072,688 | 2/1978 | Teach ................................... 548/215 |
| 4,186,130 | 1/1980 | Teach ................................... 548/215 |

*Primary Examiner*—Arthur P. Demers
*Attorney, Agent, or Firm*—Joel G. Ackerman

[57] ABSTRACT

Dichloroacetylamides selected from the group consisting of:
(a) N,N-diallyldichloroacetamide, and
(b) N-dichloroacetyl oxazolidines having the formula

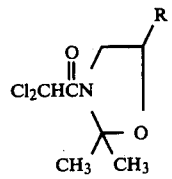

in which R is hydrogen or $C_1$-$C_3$ alkyl are produced in a continuous circulating process by reaction of dichloroacetyl chloride with respectively N,N-diallylamine or an oxazolidine having the formula

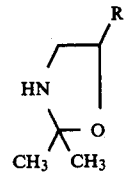

in the presence of an aqueous solution of sodium hydroxide. The conduct of this process in a continuous circulating fashion produces the desired amide in greater yield than by the heretofore practiced batch processes.

13 Claims, 1 Drawing Figure

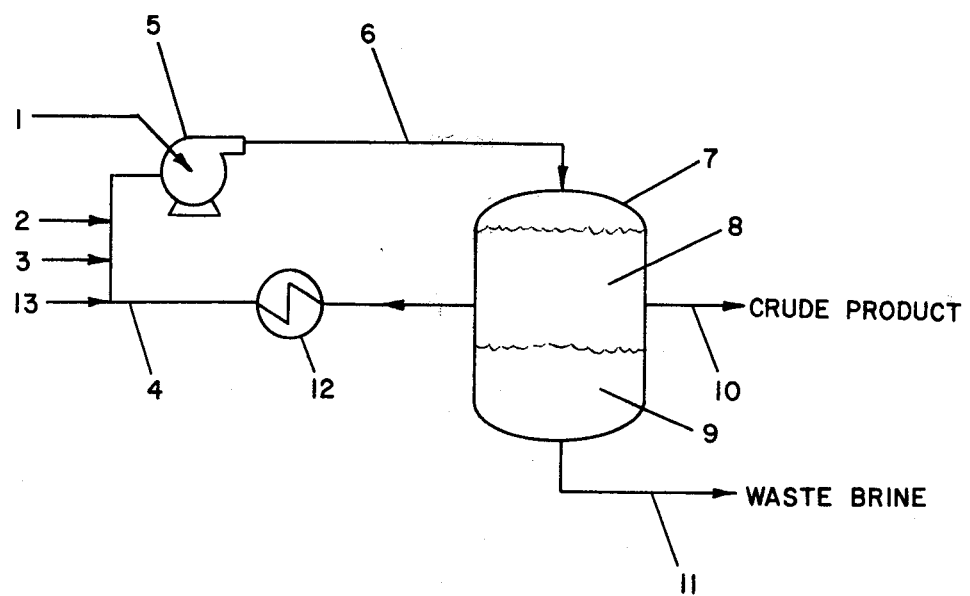

CONTINUOUS PROCESS FOR THE PRODUCTION OF DICHLOROACETAMIDES

BACKGROUND AND PRIOR ART OF THE INVENTION

This invention relates to an improved process for the production of certain dichloroacetamides. More particularly, it relates to an improved process for the production of N,N-diallyldichloroacetamide and N-dichloroacetyl oxazolidines having the formula

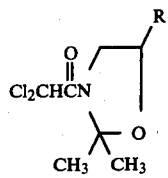

in which R is hydrogen or $C_1$–$C_3$ alkyl. The amide or oxazolidine is prepared by reaction of dichloroacetyl chloride with, respectively N,N-diallylamine or an oxazolidine having the formula

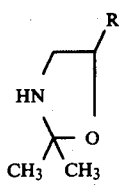

in which R is similarly hydrogen or $C_1$–$C_3$ alkyl, in the presence of an aqueous solution of sodium hydroxide.

In conducting such reactions, certain techniques have been found to be satisfactory in general in reducing the production of byproducts, particularly byproducts formed by reaction of the dichloroacetyl chloride with intermediates formed during the reaction step or the production of undesirable quantities of amine salts.

U.S. Pat. No. 3,914,302 of Jimmy Chan, et al. describes a process for the production of N,N-diallyldichloroacetamide in yields above 80% having essentially no amine salt or dichloroacetic acid as byproduct, by reaction of dichloroacetyl chloride with N,N-diallylamine in a batch process with the use of a sufficient amount of an aqueous sodium hydroxide solution having a concentration of preferably 15–50% and most preferably about 17–20%, such that at all times during the reaction, the pH of the reaction mixture remains at a value greater than 10, preferably at a value from 11 to 13. The process involves violent agitation of a mixture of the amine and aqueous sodium hydroxide, the dichloroacetyl chloride being slowly added. At the same time the temperature of the reaction mixture is maintained from about −10° to 100° C., more preferably from about 20° to about 50° C. The most preferred temperature is about 30° C.

In that process the molar ratio of dichloroacetyl chloride to diallylamine is also important and should be from about 0.7:1 to about 0.95:1. The desired amide is recovered by separation of the aqueous and organic phases, followed by stripping the organic phase to remove water and excess amine, and is said to be recovered at a rate of greater than 80% of the theoretical yield based either on diallylamine or dichloroacetyl chloride.

In U.S. Pat. No. 4,038,284 of Harold M. Pitt, there is described a process, carried out on the laboratory scale, for the production of N-substituted oxazolidines of the type mentioned above, and others. The process consists of reacting the oxazolidine with an acid chloride, for example dichloroacetyl chloride, in the presence of a hydrogen chloride acceptor and water. The preferred hydrogen chloride acceptor is sodium hydroxide, in the form of an aqueous solution containing 5 to 50%, preferably about 20%, sodium hydroxide. Reaction temperatures can range from about −5° to about +25° C. The examples illustrate that a yield of 82% of theoretical could be obtained by carrying out the process. However, such a yield required the use of a 33% sodium hydroxide solution which resulted in precipitation of solid sodium chloride.

In the production of N,N-diallylacetamide or the oxazolidine by the batch processes described in these patents, however, there can still result the formation of a substantial amount of sodium dichloroacetate by the side reaction of sodium hydroxide and dichloroacetyl chloride. This results from the contact between the sodium hydroxide solution and the dichloroacetyl chloride, which contact is increased if violent agitation is utilized, as in the process of U.S. Pat. No. 3,914,302.

N,N-diallyldichloroacetamide and the N-dichloroacetyl oxazolidines referred to are useful as herbicidal antidotes in compositions containing certain types of herbicides. An antidote is a compound which when used with a herbicide, enhances the selectivity of a herbicide towards crops, resulting in comparatively less damage or injury to a crop than when the herbicide is employed alone. The herbicide continues to function as a herbicide towards weed species.

More specifically, these compounds are useful as antidotes in combination with thiocarbamate and acetanilide herbicides.

Thiocarbamate herbicides have the formula

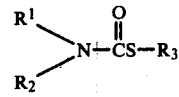

in which:
 $R_1$ is $C_1$–$C_6$ alkyl or $C_2$–$C_6$ alkenyl;
 $R_2$ is $C_1$–$C_6$ alkyl, $C_2$–$C_6$ alkenyl, cyclohexyl or phenyl; or
 $R_1$ and $R_2$ together with the nitrogen atom form a heterocyclic ring; and
 $R_3$ is $C_1$–$C_6$ alkyl, $C_1$–$C_4$ haloalkyl; $C_5$–$C_{10}$ cycloalkyl; phenyl; substituted phenyl, in which the substituents are $C_1$–$C_4$ alkyl; $C_1$–$C_4$ haloalkyl or halo; benzyl, and substituted benzyl, in which the substituents are $C_1$–$C_4$ alkyl, $C_1$–$C_4$ haloalkyl or halo.

Examples of thiocarbamate herbicides are: S-ethyldipropyl thiocarbamate, S-ethyl diisobutyl thiocarbamate, S-propyl dipropyl thiocarbamate, S-2,3,3-trichlorallyl diisopropyl thiocarbamate; S-ethyl cyclohexylethyl thiocarbamate and S-ethyl hexahydro-1H-azepine-1-carbathioate.

Acetanilide herbicides have the formula

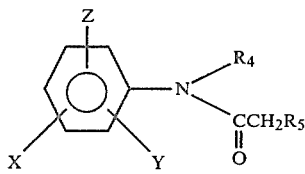

in which:

X, Y and Z are independently hydrogen or $C_1$–$C_4$ alkyl;

$R_4$ is $C_1$–$C_6$ alkyl, $C_2$–$C_{10}$ alkoxyalkyl, $C_3$–$C_6$ alkoxycarbonylalkyl and dioxolan, and $R_5$ is chlorine, bromine or iodine.

Examples of acetanilide herbicides are: 2-chloro-2',6'-diethyl-N-(methoxymethyl)acetanilide; 2-chloro-2-methyl, 6'-ethyl-N-[methoxypropyl-(2)]acetanilide; 2-chloro-2',6'-dimethyl-N-(methoxyethyl)acetanilide; 2-chloro-2'-methyl, 6'-ethyl-N-(ethoxymethyl)acetanilide; 2-chloro-N-isopropyl acetanilide; 2-chloro-2',6'-diethyl-N-(n-butoxymethyl) acetanilide; and 2-chloro-N-carbethoxymethyl-2',6'-diethyl acetanilide.

As used above:

"halo" includes fluoro, chloro, bromo and iodo;

"alkyl", "alkenyl", "haloalkyl" and "alkoxyalkyl" include both straight and branched chain moieties; and "haloalkyl" includes both mono- and polyhalogenated moieties.

Such compositions contain, in general, a herbicidally effective amount of the thiocarbamate or acetanilide herbicide and an antidotally effective amount of the N,N-diallyldichloroacetamide or N-dichloroacetyl oxazolidine.

SUMMARY OF THE INVENTION

The present invention is directed to a method for producing N,N-diallyldichloroacetamide or an N-dichloroacetyl oxazolidine as previously defined, in a continuous manner, with improved yields, as will be seen from the Examples. The improvement in yield results primarily from the formation of less byproduct sodium dichloroacetate.

In general, this invention comprises a continuous process for the production of dichloroacetamides selected from the group consisting of (a) N,N-diallyldichloroacetamide; and (b) N-dichloroacetyl oxazolidines having the formula

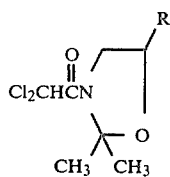

n which R is hydrogen or $C_1$–$C_3$ alkyl, by the reaction of dichloroacetyl chloride with, respectively, N,N-diallylamine or an oxazolidine having the formula

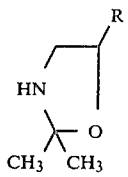

in which R is hydrogen or $C_1$–$C_3$ alkyl, in the presence of an aqueous solution of sodium hydroxide, comprising the steps of:

(a) continuously mixing the dichloroacetyl chloride, aqueous solution of sodium hydroxide and either the N,N-diallylamine or the oxazolidine by continuously introducing these substances into a circulating liquid medium to form a reaction mixture;

(b) continuously introducing the reaction mixture into a non-agitated reactor;

(c) retaining the reaction mixture in the reactor for a sufficient time for separation of the reaction mixture into an aqueous phase comprising an aqueous brine and an organic phase comprising the crude, desired product to occur;

(d) continuously withdrawing the aqueous phase from the reactor;

(e) continuously withdrawing one portion of the organic phase containing the crude product from the reactor;

(f) recovering the desired product from the portion of the organic phase withdrawn in step (e); and (g) continuously withdrawing a second portion of the organic phase from the reactor and continuously recycling it to step (a) to serve as the circulating liquid medium therein.

DESCRIPTION OF THE DRAWING

The FIGURE depicts a simplified flow sheet illustrating the conduct of the process.

DETAILED DESCRIPTION OF THE INVENTION

The process according to this invention will be described with reference to the flow sheet as shown in the FIGURE. The flow sheet is essentially the same whether the process is used to prepare N,N-diallyldichloroacetamide or an N-dichloroacetyl oxazolidine as described herein, with the exception that a solvent is employed in the production of the oxazolidine but not for N,N-diallyldichloroacetamide.

Lines 1, 2 and 3 represent feed points for respectively dichloroacetyl chloride, the N,N-diallylamine or the oxazolidine to be reacted, and an aqueous solution of sodium hydroxide. These three substances are continuously introduced at a controlled rate into a circulating organic liquid medium originating from a source hereinafter described and passing through line 4. The amine or oxazolidine and the sodium hydroxide solution may be introduced at any convenient point along line 4, and preferably at a point prior to the passage of the circulating medium through a circulation pump 5. The dichloroacetyl chloride is then introduced into the circulating mixture, most preferably by being fed into the impeller of the circulation pump 5. This method of introduction results in an intimate mixing of the three substances with each other and with the circulating medium, facilitating commencement of the desired reaction while providing reduced contact time between the sodium hydroxide and dichloroacetyl chloride.

The amine or oxaxolidine is used in sufficient excess with respect to the dichloroacetyl chloride such that in the overall reaction, the pH of the reaction mixture remains above a value of 10, preferably at a value between 11 and 13. The mole ratio of dichloroacetyl chloride to the oxazolidine is generally from about 0.50 to about 1.5, preferably from about 0.70 to about 0.85. It should be noted that, as described in the aforementioned U.S. Pat. No. 4,038,284 of Harold Pitt, the oxazolidine is preferably prepared by reaction of an alkanolamine with a carbonyl compound, and the total reaction product, which may include the oxazolidine, water of reaction, unreacted starting materials and byproducts, including a Schiff base corresponding to the oxazolidine, is introduced into the acylation step of the present process. The oxazolidine is considered to constitute about 80% of the amine constituents of such a mixture. The ratios expressed herein with respect to the oxaxolidine, in an operation of this type, take this value into consideration; they are based on a determination of the amine content of such a product multiplied by a factor of 0.8. For the production of N,N-diallyldichloroacetamide, the mole ratio of dichloroacetyl chloride to the amine is from about 0.50 to about 0.8, preferably from about 0.7 to about 0.80. In this embodiment the excess amine acts as a diluent or solvent for the amide product and no additional solvent is required.

The use of an organic solvent such as benzene or toluene is necessary in the production of N-dichloroacetyl oxazolidines by this process. Such a solvent, in an amount of 2 to 4, preferably 3 to 4 times by weight, based on the oxazolidine, may be added into the circulating medium through line 13.

The reaction mixture is conveyed through line 6 into vessel 7, which contains a liquid generally separated into organic and aqueous phases, indicated respectively as 8 and 9. The liquid medium is preferably introduced into vessel 7 by means such as a dip-tube. While the liquid may be introduced into either the aqueous phase 9 or the organic phase 8, it is preferable to introduce it into the organic phase so as to avoid undue agitation of the aqueous phase.

The organic phase 8 in vessel 7 contains primarily the crude product, that is N,N-diallyldichloroacetamide or an N-dichloroacetyl oxazolidine described above and an organic solvent, in the latter case. The aqueous phase 9 is essentially a brine solution, containing unreacted sodium hydroxide, sodium chloride, and other water-soluble materials. Two portions of the organic phase are continuously withdrawn from the reactor. One portion in line 10 is withdrawn and passed to a product recovery section (not shown). A second portion of the organic layer is withdrawn in line 4, passed through cooler 12, and recirculated as the circulating liquid medium into which the reactants are introduced. The weight ratio of the amounts of the organic layer withdrawn in the two portions, that is product and recirculating medium, is generally between about 1:50 and about 1:150 and preferably between about 1:50 and about 1:100.

The aqueous phase, that is the brine phase, is continuously withdrawn through line 11 and passed to waste disposal.

An important aspect of the process is that violent agitation is not employed in vessel 7. It is considered that violent agitation would be undesirable in that it would increase contact between the sodium hydroxide or brine phase and the dichloroacetyl chloride. By controlled addition of the reactants, with thorough mixing in the pump and good phase separation in reactor 7, side reactions such as hydrolysis of the dichloroacetyl chloride with sodium hydroxide are kept to a minimum. For this reason, reactor 7 is a non-agitated reactor; it is not equipped with any agitation means. In this fashion the amount of caustic or brine at the reaction site is minimized, although the overall amount and concentration of sodium hydroxide employed does not differ substantially from that used in the previously described processes.

The phase separation in reactor 7 occurs relatively readily and does not require a long period of time. This ease of phase separation, together with the continuous removal of the aqueous or brine-containing phase, again results in fewer side reactions and production of undesired reaction products between dichloroacetyl chloride and the caustic or brine.. The phase separation may be enhanced by passing the circulating liquid medium through a coalescer.

For the production of N,N-diallyldichloroacetamide, the process may be conducted at a temperature of from about $-10°$ C. to about $100°$ C., preferably from about $10°$ to about $30°$ C., most preferably from about $20°$ C. to about $25°$ C. To produce an N-dichloroacetyl oxazolidine the temperature may be from about $-20°$ C. to about $100°$ C., preferably from about $0°$ C. to about $15°$ C., and most preferably about $10°$ C. For both types of products, the process is preferably performed at atmospheric pressure.

The residence time in vessel 7 in maintained at about 10 to about 60 minutes, depending on the vessel volume and flow rates of materials, to achieve proper phase separation.

The rate of circulation of the liquid medium through line 4 depends on the rate of production of the desired amide or oxazolidine. The circulation rate is also maintained so as to provide a weight ratio of organic material (circulating medium and amine) to aqueous material (sodium hydroxide solution) at the point of introduction of the dichloroacetyl chloride of about 4:1–15:1, preferably from about 8:1–12:1, in the case of N,N-diallyldichloroacetamide and about 4:1–40:1, preferably about 15:1–30:1 for oxazolidines. The establishment and maintenance of this ratio ensures that the extent of contact between the dichloroacetyl chloride and sodium hydroxide will be sufficiently brief so as to minimize formation of the byproduct sodium dichloroacetate while still enabling the sodium hydroxide to perform its function of neutralizing the hydrogen chloride generated during the reaction.

For continuous operation, particularly on a commercial scale, the concentration of sodium hydroxide employed in the process should be 15–25%, preferably 18–20%.

The portion of the organic layer removed from vessel 7 in line 10 is subsequently treated to recover the desired product. For N,N-diallyldichloroacetamide, as disclosed in U.S. Pat. No. 3,914,302, recovery is effected by washing with water followed by stripping, preferably at about 100 mm mercury absolute pressure and at a temperature of about 80° C. for up to one hour, to remove water and excess amine. The purity of the product is generally about 95%, and is generally recovered in greater than 90% of theoretical yield, based on either dichloroacetyl chloride or the amine.

The oxazolidine is similarly recovered, although due to the use of a solvent, the stripping is conducted at a higher temperature, generally about 100° C. The purity is similarly generally about 95%, and the yield is 70% or greater of the theoretical amount.

The advantages and conduct of the process are further illustrated by the following examples:

EXAMPLE 1

Production of 2,2,5-trimethyl-3-dichloroacetyl oxazolidine (continuous process)

A continuous circulating system was utilized as shown in the FIGURE. Reactants and solvent were introduced at the following rates: 2,2,5-trimethyloxazolidine (line 2), 27.7 grams/minute; toluene (line 13), 86.3 grams/minute, 20% aqueous solution of sodium hydroxide (line 3), 36.4 grams/minute; dichloroacetyl chloride (line 1); 22.4 grams/minute. The molar ratio of dichloroacetyl chloride: sodium hydroxide:oxazolidine was 1.0:1.20:1.20. The liquid medium was circulated at a rate of 1 gallon/minute, producing an organic:aqueous material weight ratio at the point of introduction of the dichloroacetyl chloride of about 30:1.

The reaction temperature was maintained at about 15° C. and reaction pressure at about atmospheric.

The material was maintained in vessel 7 for a time of approximately 1.5 hours, with approximately 5 minutes required for phase separation. A brine stream was withdrawn in line 11 at a rate of 62 grams/minute and a crude product stream (line 10) at 123 grams/minute. The crude product was washed with water and stripped at a temperature of 100° C. to remove water, toluene and excess oxazolidine. The desired product, 2,2,5-trimethyl-3-dichloroacetyloxazolidine was recovered in 72% of theoretical yield, based on the dichloroacetyl chloride, and at a purity of 94%.

EXAMPLE 1A

Comparative example (batch process)

Under the same conditions, with the same rates of introduction of reactants and solvent, the desired product was obtained in 60% of theoretical yield with a purity of about 95%.

EXAMPLE 2

Production of N,N-diallyldichloroacetamide (continuous process)

A continuous circulating system, as in the FIGURE, was employed. Reactants were introduced at the following rates: dichloroacetyl chloride, 22.0 grams/minute; diallylamine, 17.4 grams/min.; 20% aqueous solution of sodium hydroxide, 35.8 grams/min. The molar ratio of acyl chloride:amine:sodium hydroxide was 1.0:1.20:1.20. The liquid medium was circulated at a rate of 1 gallon/minute, producing an organic:aqueous material weight ratio at the point of introduction of the dichloroacetyl chloride of 5.0:1.

Reaction temperature was maintained at about 30° C., and reaction pressure at about atmospheric.

The material was maintained in vessel 7 for a time of approximately 3 hours with approximately 5 minutes required for phase separation. The crude product stream (line 10) was washed with water and stripped at about 80° C. to remove water and excess amine. The desired product was obtained in 95% of theoretical yield, based on the dichloroacetyl chloride, with purity of about 95%.

EXAMPLE 2A

Comparative example (batch process)

Under the same conditions, with the same rate of introduction of reactants, the desired product was obtained in 83% of theoretical yield, with a purity of about 95%.

EXAMPLE 3

A continuous circulating system, as in the FIGURE, was employed. Reactants were introduced at the following rates: dichloroacetyl chloride, 24 grams/min.; diallylamine, 20 grams/min.; 20% aqueous solution of sodium hydroxide, 44 grams/min. The molar ratio of acyl chloride:amine:sodium hydroxide was 1.0:1.25:1.35. The liquid medium was circulated at a rate of 1 gallon/min., producing an organic:aqueous material weight ratio at the point of introduction of dichloroacetyl chloride of 4.9:1.

Reaction temperature was maintained at about 28° C., and reaction pressure at about atmospheric.

The crude product was removed and treated as in Example 2. In three runs under these conditions, the desired product was produced in yields ranging from 89% to 100% of theoretical, based on the acyl chloride, with purities ranging from 95 to 96%.

EXAMPLE 3A

Comparative example (continuous process)

Operation of the process as in Example 3 was performed with a molar ratio of acyl chloride:amine:sodium hydroxide of 1.0:1.17:1.20. The smaller quantity of amine resulted in poor phase separation.

EXAMPLE 3B

Comparative example (batch process)

Operation of the process as in Example 3A resulted in production of the desired product in 82% of theoretical yield with a purity of 95%.

What is claimed is:

1. A continuous process for the production of dichloroacetamides selected from the group consisting of
   (a) N,N-diallyldichloroacetamide; and
   (b) N-dichloroacetyl oxazolidines having the formula

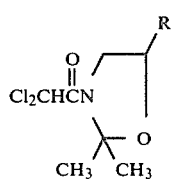

in which R is hydrogen or $C_1$–$C_3$ alkyl, by reaction of dichloroacetyl chloride with, respectively, N,N-diallylamine or an oxazolidine having the formula

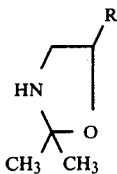

in which R is hydrogen or $C_1$–$C_3$ alkyl, in the presence of an aqueous solution of sodium hydroxide, comprising the steps of:

(a) continuously mixing the dichloroacetyl chloride, aqueous solution of sodium hydroxide and either N,N-diallylamine or the oxazolidine by continuously introducing these substances into a circulating liquid medium to form a reaction mixture;

(b) continuously introducing the reaction mixture into a non-agitated reactor;

(c) retaining the reaction mixture in the reactor for a sufficient time such that there occurs separation of the mixture into an aqueous phase comprising brine and an organic phase comprising the crude desired product;

(d) continuously withdrawing the aqueous phase from the reactor;

(e) continuously withdrawing one portion of the organic phase containing N,N-diallyldichloroacetamide, or an N-dichloroacetylated oxazolidine from the reactor;

(f) recovering the desired product from the organic phase withdrawn in step (e); and (g) continuously withdrawing a second portion of the organic phase from the reactor and continuously recycling it to step (a) to serve as the circulating liquid medium therein.

2. A process according to claim 1 in which N,N-diallylamine is a reactant and N,N-diallyldichloroacetamide is the desired product.

3. A process according to claim 2 in which the mole ratio of dichloroacetyl chloride to diallylamine is between about 0.50 and about 0.8.

4. A process according to claim 1 in which an oxazolidine is a reactant and an N-dichloroacetyl oxazolidine is the desired product.

5. A process according to claim 4 in which the mole ratio of dichloroacetyl chloride to the oxazolidine is between about 0.50 and about 1.5.

6. A process according to claim 4 in which the desired product is an N-dichloroacetyl oxazolidine in which R is hydrogen.

7. A process according to claim 4 in which the desired product is an N-dichloroacetyl oxazolidine in which R is methyl.

8. A process according to claim 4 in which the desired product is an N-dichloroacetyl oxazolidine in which R is n-propyl.

9. A process according to claim 1 in which the concentration of sodium hydroxide is from about 15 to about 25%.

10. A process according to claim 1 in which the concentration of sodium hydroxide is from about 18 to about 20%.

11. A process according to claim 1 in which the circulation of the liquid medium in step (g) is controlled so as to produce a weight ratio of organic to aqueous material at the point of introduction of the dichloroacetyl chloride of from about 4:1 to about 40:1.

12. A process according to claim 11 in which the weight ratio of organic to aqueous material is from about 8:1 to about 12:1.

13. A process according to claim 1 in which the pH of the reaction system is maintained at a value greater than 10.

* * * * *